(12) United States Patent
Filippi et al.

(10) Patent No.: US 7,959,678 B2
(45) Date of Patent: Jun. 14, 2011

(54) INTERVERTEBRAL DISK IMPLANT

(75) Inventors: Michael Filippi, Schaffhausen (CH);
Mathias Heller, Raeterschen (CH); Jörn Seebeck, Winterthur (CH); Guido Casutt, Rickenbach (CH)

(73) Assignee: Zimmer GmbH, Winterthur (CH)

( * ) Notice: Subject to any disclaimer, the term of this patent is extended or adjusted under 35 U.S.C. 154(b) by 1825 days.

(21) Appl. No.: 11/107,579

(22) Filed: Apr. 15, 2005

(65) Prior Publication Data
US 2005/0261772 A1    Nov. 24, 2005

(30) Foreign Application Priority Data

May 18, 2004  (DE) .................... 10 2004 024 662
Nov. 17, 2004  (EP) ........................... 04027322

(51) Int. Cl.
*A61F 2/44*    (2006.01)
(52) U.S. Cl. .................................... 623/17.14
(58) Field of Classification Search ..... 623/17.11–17.16
See application file for complete search history.

(56) References Cited

U.S. PATENT DOCUMENTS

| | | |
|---|---|---|
| 4,759,766 A | 7/1988 | Buettner-Janz et al. |
| 4,759,769 A | 7/1988 | Hedman et al. |
| 4,997,432 A | 3/1991 | Keller |
| 5,314,477 A | 5/1994 | Marnay |
| 5,401,269 A | 3/1995 | Buttner-Janz et al. |
| 5,425,773 A | 6/1995 | Boyd et al. |
| 5,534,029 A | 7/1996 | Shima |
| 5,556,431 A | 9/1996 | Buttner-Janz |
| 5,562,738 A | 10/1996 | Boyd et al. |
| 5,674,294 A | 10/1997 | Bainville et al. |
| 5,674,296 A | 10/1997 | Bryan et al. |
| 5,683,465 A | 11/1997 | Shinn et al. |
| 5,888,226 A | 3/1999 | Rogozinski |
| 5,893,889 A | 4/1999 | Harrington |
| 5,895,428 A | 4/1999 | Berry |
| 5,928,284 A | 7/1999 | Mehdizadeh |
| 5,989,291 A | 11/1999 | Ralph et al. |
| 6,063,121 A | 5/2000 | Xavier et al. |
| 6,375,682 B1 | 4/2002 | Fleischmann et al. |
| 6,416,551 B1 | 7/2002 | Keller |
| 6,468,310 B1 | 10/2002 | Ralph et al. |
| 6,517,580 B1 | 2/2003 | Ramadan et al. |
| 6,527,806 B2 | 3/2003 | Ralph et al. |

(Continued)

FOREIGN PATENT DOCUMENTS

AT    006369 U1    9/2003

(Continued)

OTHER PUBLICATIONS

European Patent Office, Partial European Search Report in related Application No. 07008698.8-2310, dated Jul. 31, 2007 (8 pages).

*Primary Examiner* — Eduardo C Robert
*Assistant Examiner* — Tara R Carter
(74) *Attorney, Agent, or Firm* — Seager, Tufte & Wickhem, LLC

(57) ABSTRACT

The invention relates to an intervertebral disk implant having two implant plates contacting prepared vertebral body surfaces in the implanted state and an implant core which can be introduced between the implant plates. The invention further relates to a method for the manufacture of an intervertebral disk implant.

38 Claims, 9 Drawing Sheets

U.S. PATENT DOCUMENTS

Figure 2A:
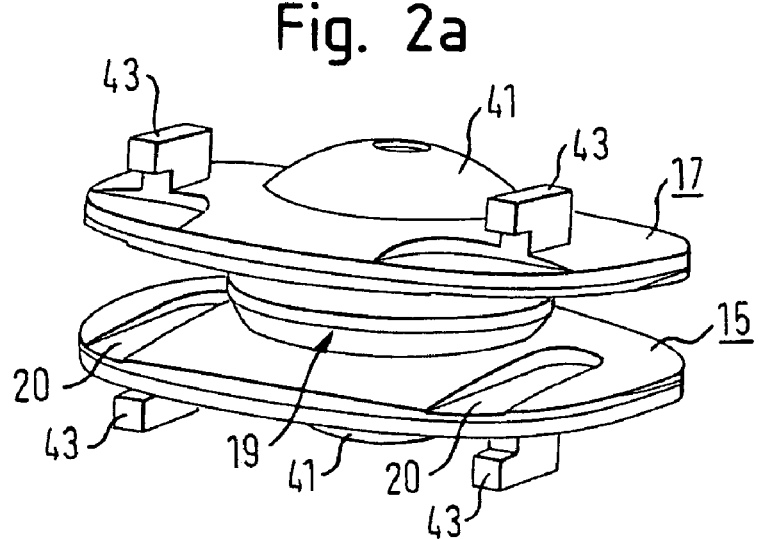

| | | | |
|---|---|---|---|
| 6,572,653 B1 | 6/2003 | Simonson | |
| 6,579,321 B1 | 6/2003 | Gordon et al. | |
| 6,582,466 B1 | 6/2003 | Gauchet | |
| 6,682,562 B2 | 1/2004 | Viart et al. | |
| 6,692,495 B1 | 2/2004 | Zacouto | |
| 6,706,068 B2 | 3/2004 | Ferree | |
| 6,733,532 B1 | 5/2004 | Gauchet et al. | |
| 6,740,117 B2 | 5/2004 | Ralph et al. | |
| 6,793,678 B2 | 9/2004 | Hawkins | |
| 6,936,071 B1 | 8/2005 | Marnay et al. | |
| 7,025,787 B2 | 4/2006 | Bryan et al. | |
| 7,250,060 B2 | 7/2007 | Trieu | |
| 7,531,001 B2 | 5/2009 | De Villiers et al. | |
| 7,695,517 B2 * | 4/2010 | Benzel et al. | 623/17.15 |
| 2002/0082608 A1 | 6/2002 | Reiley et al. | |
| 2002/0111681 A1 | 8/2002 | Ralph et al. | |
| 2002/0128715 A1 * | 9/2002 | Bryan et al. | 623/17.15 |
| 2003/0009223 A1 | 1/2003 | Fehling et al. | |
| 2003/0009226 A1 | 1/2003 | Graf | |
| 2003/0014111 A1 | 1/2003 | Ralph et al. | |
| 2003/0045939 A1 | 3/2003 | Casutt | |
| 2003/0045940 A1 | 3/2003 | Eberlein et al. | |
| 2003/0055427 A1 | 3/2003 | Graf | |
| 2003/0135277 A1 | 7/2003 | Bryan et al. | |
| 2003/0176923 A1 | 9/2003 | Keller et al. | |
| 2003/0191533 A1 | 10/2003 | Dixon et al. | |
| 2003/0191534 A1 | 10/2003 | Viart et al. | |
| 2003/0195631 A1 | 10/2003 | Ferree | |
| 2003/0199981 A1 | 10/2003 | Ferree | |
| 2003/0204260 A1 | 10/2003 | Ferree | |
| 2003/0204261 A1 | 10/2003 | Eisermann et al. | |
| 2003/0204271 A1 | 10/2003 | Ferree | |
| 2003/0216810 A1 | 11/2003 | Ralph et al. | |
| 2003/0220691 A1 | 11/2003 | Songer et al. | |
| 2003/0233097 A1 | 12/2003 | Ferree | |
| 2004/0002759 A1 | 1/2004 | Ferree | |
| 2004/0002761 A1 | 1/2004 | Rogers et al. | |
| 2004/0002762 A1 | 1/2004 | Hawkins | |
| 2004/0030390 A1 | 2/2004 | Ferree | |
| 2004/0030391 A1 | 2/2004 | Ferree | |
| 2004/0068318 A1 | 4/2004 | Coates et al. | |
| 2004/0068321 A1 | 4/2004 | Ferree | |
| 2004/0073307 A1 | 4/2004 | Keller | |
| 2004/0073311 A1 | 4/2004 | Ferree | |
| 2004/0073313 A1 | 4/2004 | Link et al. | |
| 2004/0083000 A1 | 4/2004 | Keller et al. | |
| 2004/0093082 A1 | 5/2004 | Ferree | |
| 2004/0093087 A1 | 5/2004 | Ferree et al. | |
| 2004/0117021 A1 | 6/2004 | Biedermann et al. | |
| 2004/0117022 A1 | 6/2004 | Marnay et al. | |
| 2004/0127991 A1 | 7/2004 | Ferree | |
| 2004/0133278 A1 | 7/2004 | Marino et al. | |
| 2004/0138753 A1 | 7/2004 | Ferrii | |
| 2004/0143332 A1 | 7/2004 | Krueger et al. | |
| 2004/0143334 A1 | 7/2004 | Ferree | |
| 2004/0153157 A1 | 8/2004 | Keller | |
| 2004/0167626 A1 | 8/2004 | Geremakis et al. | |
| 2004/0172021 A1 | 9/2004 | Khalili | |
| 2004/0186577 A1 | 9/2004 | Ferree | |
| 2004/0193273 A1 | 9/2004 | Huang | |
| 2004/0215342 A1 | 10/2004 | Suddaby | |
| 2004/0220672 A1 | 11/2004 | Shadduck | |
| 2004/0243238 A1 | 12/2004 | Arnin et al. | |
| 2004/0243241 A1 | 12/2004 | Istephanous et al. | |
| 2005/0004572 A1 | 1/2005 | Biedermann et al. | |
| 2006/0009850 A1 | 1/2006 | Frigg et al. | |
| 2006/0036325 A1 | 2/2006 | Paul et al. | |
| 2006/0190082 A1 | 8/2006 | Keller et al. | |
| 2006/0235524 A1 | 10/2006 | Petit et al. | |
| 2006/0235527 A1 | 10/2006 | Buettner-Janz et al. | |
| 2006/0259144 A1 | 11/2006 | Trieu | |
| 2007/0162137 A1 | 7/2007 | Kloss et al. | |
| 2008/0065078 A1 | 3/2008 | Graf | |
| 2009/0177284 A1 | 7/2009 | Rogers et al. | |

FOREIGN PATENT DOCUMENTS

| | | |
|---|---|---|
| DE | 2031043 A | 11/1971 |
| DE | 2263842 A | 7/1974 |
| DE | 2804936 A1 | 8/1979 |
| DE | 3023353 A1 | 4/1981 |
| DE | 239523 A1 | 10/1986 |
| DE | 4213771 C1 | 9/1993 |
| DE | 29916078 U1 | 12/1999 |
| DE | 20310432 U1 | 10/2003 |
| DE | 20310433 U1 | 10/2003 |
| DE | 20313183 U1 | 11/2003 |
| DE | 20315611 U1 | 1/2004 |
| DE | 009542 U1 | 9/2004 |
| DE | 20320454 U1 | 11/2004 |
| EP | 0176728 B1 | 7/1989 |
| EP | 0560140 A1 | 9/1993 |
| EP | 0560141 B1 | 9/1993 |
| EP | 0699426 B1 | 3/1996 |
| EP | 0747025 B1 | 12/1996 |
| EP | 0955021 B1 | 11/1999 |
| EP | 1214918 A1 | 6/2002 |
| EP | 0892627 B1 | 8/2003 |
| EP | 1344506 A1 | 9/2003 |
| EP | 1346709 B1 | 9/2003 |
| EP | 1374807 A1 | 1/2004 |
| EP | 1 405 615 B1 | 4/2004 |
| EP | 1437101 A2 | 7/2004 |
| EP | 1475059 A2 | 11/2004 |
| EP | 1532948 A1 | 5/2005 |
| EP | 1857079 B1 | 8/2009 |
| EP | 1549260 B1 | 1/2010 |
| FR | 2372622 A | 12/1976 |
| FR | 2718635 A1 | 10/1995 |
| FR | 2730159 A1 | 8/1996 |
| FR | 2734148 A1 | 11/1996 |
| FR | 2775587 A1 | 9/1999 |
| FR | 2787017 A1 | 6/2000 |
| FR | 2851157 A1 | 8/2004 |
| JP | 61122859 A | 6/1986 |
| JP | 63164948 A | 8/1988 |
| JP | 2003526456 A | 9/2003 |
| JP | 2004097823 A | 4/2004 |
| WO | WO 93/10725 A2 | 6/1993 |
| WO | WO 94/04100 A1 | 3/1994 |
| WO | WO 95/19153 A1 | 7/1995 |
| WO | WO 98/14142 A1 | 4/1998 |
| WO | WO 99/05995 A1 | 2/1999 |
| WO | WO 99/53871 A1 | 10/1999 |
| WO | WO 00/04851 A1 | 2/2000 |
| WO | WO 00/13619 A1 | 3/2000 |
| WO | WO 00/13620 A1 | 3/2000 |
| WO | WO 00/42944 A1 | 7/2000 |
| WO | WO 00/53127 A1 | 9/2000 |
| WO | WO 00/74606 A1 | 12/2000 |
| WO | WO 01/01893 A1 | 1/2001 |
| WO | WO 01/15638 A1 | 3/2001 |
| WO | WO 01/19295 A1 | 3/2001 |
| WO | WO 01/93785 A2 | 12/2001 |
| WO | WO 01/93786 A2 | 12/2001 |
| WO | WO 02/11650 A2 | 2/2002 |
| WO | WO 02/47586 A1 | 6/2002 |
| WO | WO 02/085227 A1 | 10/2002 |
| WO | WO 02/085261 A1 | 10/2002 |
| WO | WO 02/089701 A2 | 11/2002 |
| WO | WO 03/003952 A1 | 1/2003 |
| WO | WO 03/007779 A2 | 1/2003 |
| WO | WO 03/007780 A2 | 1/2003 |
| WO | WO 03/028583 A2 | 4/2003 |
| WO | WO 03/032801 A2 | 4/2003 |
| WO | WO 03/032802 A2 | 4/2003 |
| WO | 03063727 | 8/2003 |
| WO | WO 03/075804 A1 | 9/2003 |
| WO | WO 03/084449 A1 | 10/2003 |
| WO | WO 03/090650 A1 | 11/2003 |
| WO | WO 03/094806 A1 | 11/2003 |
| WO | WO 2004/016217 A2 | 2/2004 |
| WO | WO 2004/026187 A1 | 4/2004 |
| WO | WO 2004/028415 A1 | 4/2004 |
| WO | WO 2004/037131 A1 | 5/2004 |

| | | |
|---|---|---|
| WO | WO 2004/039291 A1 | 5/2004 |
| WO | WO 2004/041129 A1 | 5/2004 |
| WO | WO 2004/041131 A2 | 5/2004 |
| WO | WO 2004/047691 A1 | 6/2004 |
| WO | WO 2004/054475 A1 | 7/2004 |
| WO | WO 2004/054476 A1 | 7/2004 |
| WO | WO 2004/054477 A1 | 7/2004 |
| WO | WO 2004/054478 A1 | 7/2004 |
| WO | WO 2004/066884 A1 | 8/2004 |
| WO | WO 2004/073561 A1 | 9/2004 |
| WO | WO 2004/084774 A1 | 10/2004 |
| WO | WO 2004/089224 A2 | 10/2004 |
| WO | WO 2004/089258 A1 | 10/2004 |
| WO | WO 2004/089259 A1 | 10/2004 |
| WO | WO 2004/098466 A2 | 11/2004 |
| WO | 2005072660 A1 | 8/2005 |

* cited by examiner

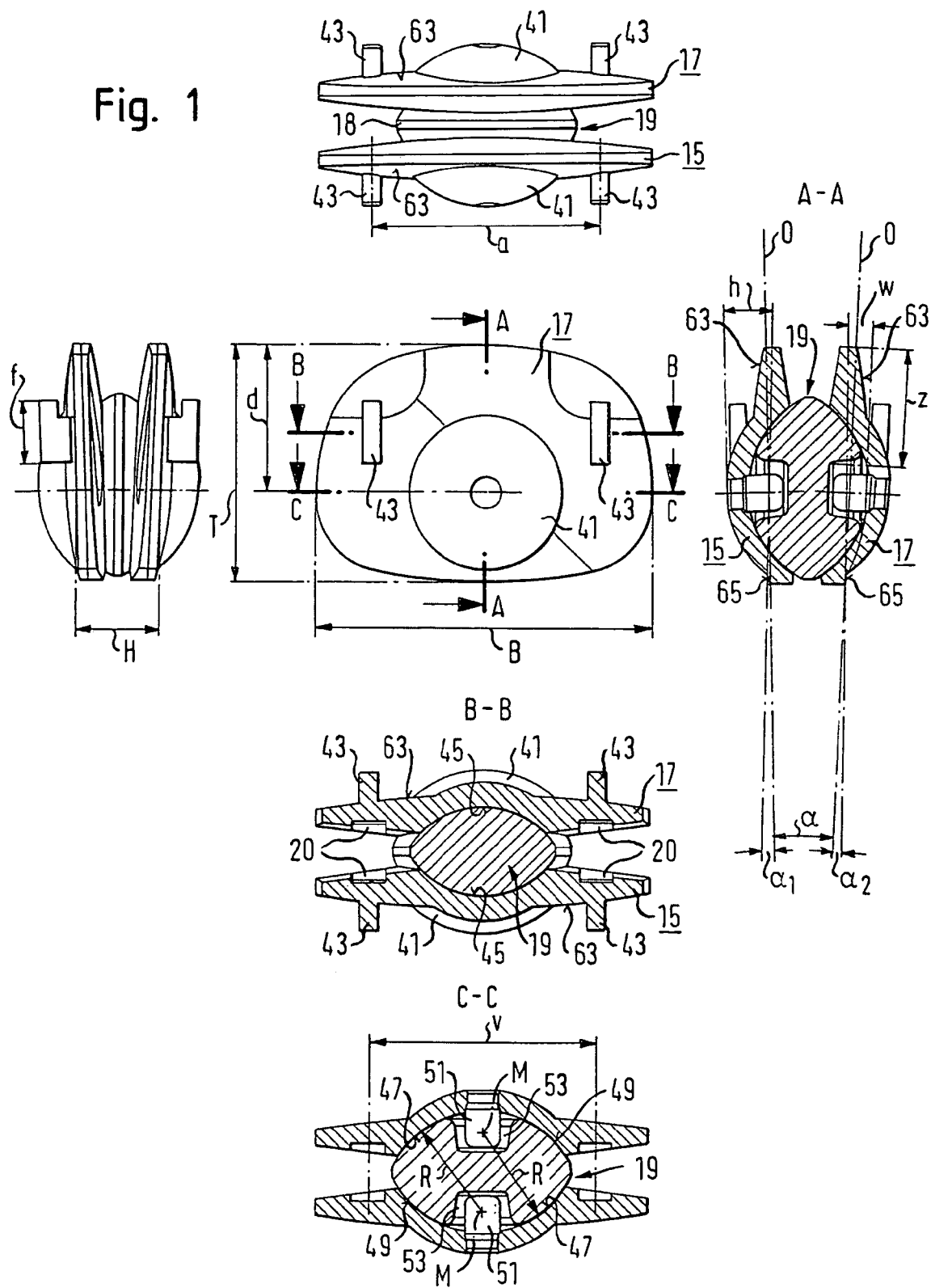

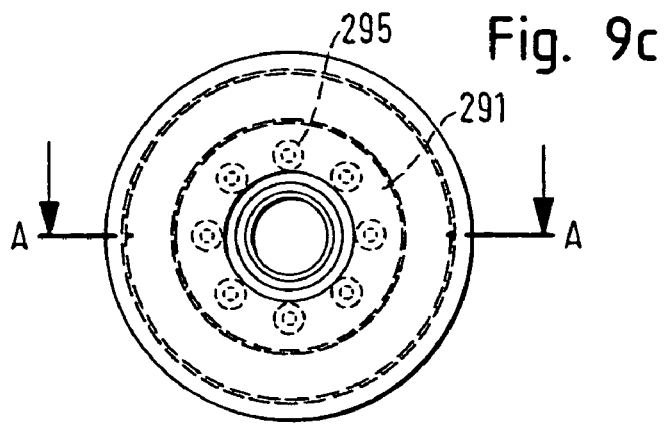
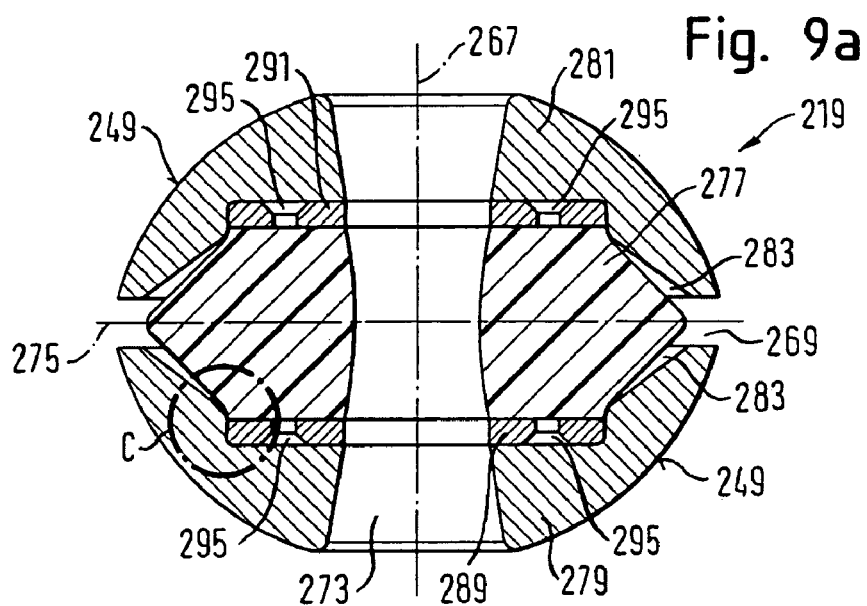
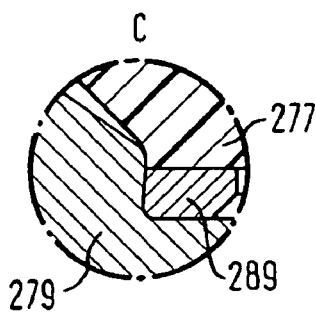
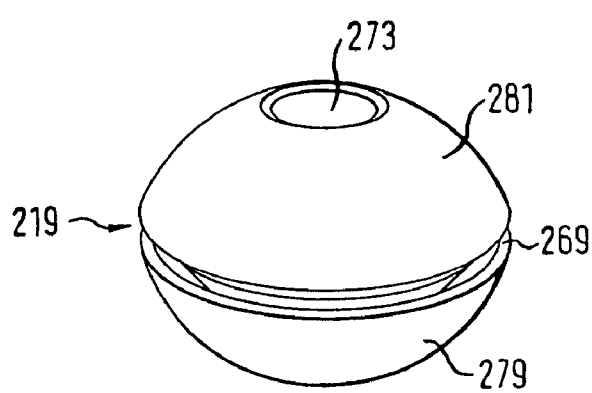

INTERVERTEBRAL DISK IMPLANT

The invention relates to an intervertebral disk implant and to a method for its manufacture.

Artificial intervertebral disks have to satisfy a plurality of demands and, in this process, do not only have to come as close as possible to the behavior of a natural intervertebral disk, but must, for example, also be usable in as simple a manner as possible, i.e. must be able to be introduced between the respective two adjacent vertebral bodies, and have to have good biocompatibility with respect to the materials used. In particular the reproduction of a resilient or dynamic behavior which is as natural as possible under different pressure conditions, which occur under the normal movements of the spinal column which also bring about extreme strains, has proved to be difficult in the design of intervertebral disk implants.

It is the object of the invention to provide an intervertebral disk implant which satisfies all substantial demands in the best possible manner and which in particular comes as close as possible to a natural intervertebral disk with respect to the resilient or dynamic behavior.

This object is satisfied by the features of claim 1 and in particular in that the intervertebral disk implant includes two implant plates, which contact prepared surfaces of intervertebral bodies in the implanted state, as well as an implant core which can be introduced between the implant plates.

Such an intervertebral disk implant provides a plurality of possibilities to influence the dynamic or resilient behavior in the respectively desired manner, for example by shaping or material choice. The intervertebral disk implant in accordance with the invention furthermore proves to be particularly advantageous with respect to the introduction between two adjacent vertebral bodies. Reference is made in this respect to the European patent application EP 03 026 582 which was filed on Nov. 18, 2003 and whose priority is claimed for the present application. This priority application relates, among other things, to an operation system for the insertion of intervertebral disk implants. This operation system and the operation itself are, however, not the subject of the present application so that they will not be looked at in any more detail.

Advantageous embodiments of the invention can also be seen from the dependent claims, from the description and from the drawing.

The implant core preferably has a lens-like basic shape. The implant core can in particular have at least approximately the shape of two spherical segments whose planar sides lie on top of one another, with the respective spherical center of the one spherical segment lying within the other spherical segment. Alternatively, provision can be made for the implant core to have at least approximately the shape of two spherical segments whose planar sides face one another and of a cylindrical disk lying between them, with—as in the aforesaid alternative—the spherical center of the one spherical center lying within the other spherical segment.

Investigations making use of model calculations have surprisingly shown that local load peaks of the implant core can be avoided, in particular while maintaining the rotational symmetry, if specific adaptations of the geometry of the implant core are made. It has in particular been found that the peak loads can be reduced by up to 30% with an implant core directly adapted with respect to the geometry in comparison with an implant core whose articulation surfaces are in full-surface contact with the articulation surfaces of the implant plates when the implant has been assembled. Abrasion effects and wear phenomena at the cooperating articulation surfaces are hereby noticeably reduced.

It has in particular been found that the desired load reductions can be achieved by an improved "spring effect" of the implant core put under pressure via the implant plates.

Accordingly, in accordance with a preferred embodiment of the invention, it is proposed that the implant core has a basic shape of two spherical segments whose planar sides lie on top of one another or face one another and is provided by material removal from the basic shape with at least one spring region which gives the implant core increased resilient shape changeability with respect to the basic shape under the effect of pressure.

It is particularly preferred for the articulation surfaces of the implant core and of the implant plates to contact one another in linear or strip shape when the intervertebral disk implant is assembled.

An advantage of such an embodiment lies in the fact that hollow spaces filled with liquid between the outer surface of the implant core and the counter surfaces of the implant plates, which are sealed by a contact of implant core and implant plates, can bring about or support an advantageous hydrostatic support effect in that the effective support surface is expanded to the whole inner region.

In a particularly preferred practical embodiment, the articulation surfaces of the implant plates are each provided in the form of a part surface of a sphere having a constant radius of curvature, with the articulation surfaces of the implant core each being formed by a plurality of part surfaces of a sphere having different radii of curvature. The articulation surfaces of the implant plates are preferably each formed by two part surfaces whose radii of curvature are smaller than the radius of curvature of the articulation surfaces of the implant plates and which start from a contact line between the implant core and the implant planes in the direction of the core pole, on the one hand, and in the direction of the core equator, on the other hand.

Provision can alternatively or additionally be made for the implant core to be provided, in particular in the region of its equatorial plane, with an outer ring groove and/or with an inner ring groove preferably forming a radial extension of a passage extending perpendicular to the equatorial plane.

Spring regions likewise resulting in a reduction of peak loads are created by such a material removal, on the basis of which the implant core can be deformed in a directly presettable manner under the effect of pressure.

It is preferred for the implant core to have a passage extending perpendicular to the equatorial plane. The afore-mentioned load calculations have shown that the peak loads can be reduced by the explained measures irrespective of whether such a passage is present or not. Nevertheless, such a passage provides a further possibility of optimizing the implant geometry.

Complex investigations which make use of model calculations and trials have furthermore shown that specific spatial distributions of the resilience of the implant core prove to be particularly advantageous. It can be achieved by a skillful choice of the dependence of the resilient behavior or spring effect of the implant core on the radial spacing to its center or central axis that no unacceptably high specific pressure loads occur at any point of the articulation surfaces of the implant core cooperating with the articulation surfaces of the implant plates. It can in particular be achieved that pressure peaks are avoided in the radially outer region. In this manner, it is possible to successfully counteract wear to the articulation surfaces which brings along the risk of material abrasion to be avoided in every case.

Provision is made in accordance with a preferred embodiment of the invention for the implant core to have a greater resilience in a radially outer rim region than in a radially inner central region. Provision can furthermore be made for the implant core to have the lowest resilience and thus the greatest stiffness in a radially central region which is disposed between a radially outer region, on the one hand, and a central region provided with a passage extending perpendicular to an equatorial plane, on the other hand.

In accordance with a particularly preferred embodiment of the invention, the implant core is made in multiple parts. An arrangement is in particular provided of at least one inner support cushion and at least one shell surrounding the support cushion. The support cushion can damp axial movements of the shell cooperating directly with the implant plates. The support cushion can in particular prevent disadvantageous pressure peaks in the radially outer rim region and—where present—in the region of an inner side bounding a central passage, for example by the manner of its inner support or by its shape. This multi-part design has the advantage that the arising of damaging abrasion is prevented or is at least reduced by a sufficiently large amount even with materials used for the implant core which have a comparatively low wear resistance.

The support cushion preferably has a lens-shaped basic shape.

Provision is furthermore preferably made for the shell to include two half shells which are preferably arranged spaced apart from one another in the axial direction.

Provision is furthermore preferably made for the support cushion and the shell to be made from different materials. The material of the shell is preferably harder and/or stiffer than the material of the support cushion.

A particularly preferred material for the support cushion is polycarbonate urethane (PCU). This material is particularly well-suited to achieve a desired maximum "spring path" of the implant core of approximately 1 mm. Alternatively, e.g. silicone or a mixture of PCU and silicone correspondingly adjusted to the desired resilient properties of the support cushion can also be provided as the material for the support cushion.

Although it is in principle possible in accordance with the invention to manufacture the implant core from a suitable material such as in particular PCU, instead of having a multi-part design of the implant core, and to prevent excessive pressure loads solely by a skillful shape, in particular in the axial outer rim regions, it is nevertheless preferred to, so-to-say, "enhance" the articulation surfaces and, for this purpose, to use the mentioned shell surrounding the support cushion at least partly or the half shells. Polyethylene (PE), highly cross-linked polyethylene, UHMWPE (UHMW=ultra-high molecular weight) or metal, in particular a CoCrMo alloy or a titanium alloy, are preferably considered as the material for the shell. The biocompatibility can in particular be ensured by such materials.

If, in accordance with a further preferred embodiment, the support cushion has its lowest resilience or its largest stiffness approximately in the center between the radially outer rim region and a central region, disadvantageous turning inside-out arrangements of the half shells which are formed in ring shape on the presence of a central passage can be avoided.

It is furthermore proposed in accordance with the invention for the shell to project beyond the support cushion in the radial direction. It is achieved by this "overhang" of the shell or of the two half shells with respect to the inner support cushion that the actual support of the implant plates is transposed via the shell or half shells in the direction of a central region between the axially outer rim region and a central region and, in this manner, pressure peaks are prevented, or at least greatly reduced, in the rim region or the central region.

In particular in the radially outer rim region of the implant core, a respective intermediate space can be provided between the shell or the half shells, on the one hand, and the support cushion, on the other hand, such that no support of the shell at the support cushion takes place in this region.

In accordance with a further embodiment of the invention, an intermediate layer, in particular made of metal, is arranged between the support cushion and the shell. The extent of this intermediate layer can generally be selected as desired. The intermediate layer can thus, for example, extend parallel to the equatorial plane or be curved in accordance with the outer shell.

If such an intermediate layer is present, which can consist of two separate individual layers each associated with a half shell, provision can then furthermore be made for the shell or the half shells to be supported at the inner support cushion exclusively via this intermediate layer or individual layers, i.e. material contact takes place exclusively between the shell and the intermediate layer, but not between the shell and the support cushion.

The intermediate layer can be made as a path boundary for spigots of the implant plates projecting into a passage extending perpendicular to an equatorial plane. An impairment of the outer shell preferably consisting of PE is hereby avoided in an advantageous manner.

Provision is furthermore preferably made for a passage of the implant core extending perpendicular to an equatorial plane to have a cross-sectional surface varying over its length. The cross-sectional surface preferably respectively increases, in particular constantly, from the equatorial plane to the outside. The pressure behavior, in particular of the inner support cushion, can be set directly by the shape of the central passage.

A further possibility of setting the pressure behavior of the implant core lies, in accordance with a further preferred embodiment of the invention, in the fact of stiffening the support cushion in the axial direction in a central region. Alternatively or additionally, the support cushion can be inwardly stiffened in the radial direction in the event of the provision of a central passage.

In particular a separate stiffening element, preferably having a ring-shaped or cylindrical base shape, can be provided for the stiffening of the support cushion. This stiffening element can be arranged in the central passage and be made, for example, as so-called metal bellows.

Such a stiffening element can not only increase the stiffness of the support cushion in the central region or at the inner rim region of the support cushion bounding the central passage, but can simultaneously also support the support cushion in the radial direction, whereby the stiffness of the support cushion in the central region is likewise enlarged.

A stiffening element made, for example, as metal bellows moreover offers the advantageous possibility to better guide the half shells surrounding the support cushion at least in part and made in ring shape in the case of a central passage, whereby a "floating" of the half shells on the support cushion is avoided.

In a preferred embodiment of the invention, the support cushion is injection molded onto the shell or the half shells, with the material of the support cushion having a higher melting point than the material of the shell, preferably for the forming of a material composite between the support cushion and the shell which can be established by the injection molding. The manufacture of the intervertebral disk implant in accordance with the invention will be looked at in more detail at another point.

Provision can also be made for the support cushion to be injection molded onto the intermediate layer when an intermediate layer as explained above is used.

It is furthermore proposed in accordance with the invention to connect the support cushion or an intermediate layer connected to the support cushion, and in particular made of metal, to the shell or to the half shells by a clip, snap, or latch connection.

As regards the implant plates of the implant in accordance with the invention, provision is preferably made in accordance with the invention for the implant plates each to have a dome-shaped extension, in particular in the shape of a spherical segment, or a barrel-shaped extension on their outer side. These domes or barrels provide a primary positional stability of the implant after the insertion, with a barrel-shaped extension moreover being able to satisfy a guide function during the insertion.

Furthermore, in accordance with the invention, it is proposed that the outer sides of the implant plates are each outwardly arched. These arches are preferably provided in addition to the aforementioned dome-shaped or barrel-shaped extensions, and indeed such that in each case the arch is shallower, but in contrast has a larger extent in the plane of the plate than the dome or the barrel.

Furthermore, provision can be made in accordance with the invention for the outer sides of the implant plates each to have a planar rim region extending at least over part of the periphery of the implant plates.

Overall, a contour-optimized interface to the osseous composition of the vertebral body can be achieved by an embodiment of the outer sides of the implant plates in each case with a comparatively strongly curved, dome-shaped or barrel-shaped extension, a relatively shallow arch and a planar rim region.

Furthermore, the implant plates can each have at least one guide projection, in particular formed as a peen, and/or a holding projection, in particular a pyramid-shaped holding projection, on their outer sides. The implant is hereby given rotational stability in the inserted state, with the holding projections additionally being able to give the inserted implant security against slipping out.

Provision is made in a particularly preferred embodiment for the implant plates each to have a recess on their inner sides for the reception of the implant core, with the cooperating articulation surfaces of the recess and of the implant core each being part surfaces of a sphere. The recesses permit a countersunk arrangement, and so an arrangement secure against slipping out, of the implant core between the implant plates. By forming the articulation surfaces as part surfaces of a sphere, the intervertebral disk implant in accordance with the invention is rotationally symmetrical with respect to its movement possibilities.

To reliably prevent a slipping out of the implant core from the reception space formed by the recesses or concavities of the implant plates with extreme body postures, provision can be made for at least one implant plate to have a spigot which protrudes from its inner side and which projects into a depression formed on the outer side of the implant core when the implant is put together, with the depression being dimensioned larger than the spigot in order to permit a relative movement between the implant plate and the implant core.

The spigot and/or the center of the implant core can be arranged either centrally or eccentrically with respect to the dimension of the implant plate in the sagittal direction.

To keep the required traction amount for the introduction of the implant core between the implant plates as low as possible, provision can be made in accordance with a further embodiment for the implant core to be provided with an introductory passage for the spigot of the implant plate extending from the margin to the depression on at least one outer side.

An alternative or additional possibility to keep the traction amount low consists, in accordance with a further embodiment, of the fact of providing at least one implant plate—on its inner side—with an introductory passage for the implant core extending from the rim to the recess.

The invention also relates to a method for the manufacture of an intervertebral disk implant which includes two implant plates contacting prepared vertebral body surfaces in the implanted state and an implant core which can be introduced between the implant plates and includes at least one inner support cushion and at least one shell surrounding the support cushion and preferably formed by two half shells, with the support cushion being injection molded onto the shell, in particular onto the half shells, in a plastic injection molding method, or being injection molded onto an intermediate layer arranged between the support cushion and the shell in the finished state.

A material for the support cushion to be injection molded is preferably selected for the manufacture of a material composite between the support cushion and the shell which has a higher melting point than the material of the shell. As already explained above, a preferred material for the support cushion is polycarbonate urethane (PCU), silicone or a mixture of PCU and silicone, whereas polyethylene (PE), highly cross-linked PE, UHMWPE or metal is preferably used for the shell. Whereas the melting point of PCU lies above 200° C., the melting point of PE lies in the range of 120° C. It was found that half shells manufactured from PE can nevertheless be injection molded from PCU using a cooled injection mold such that a suitable material composite is created.

This material composite can be improved in that recesses or undercuts formed at the inner side of the half shells are filled on the injection molding of the support cushion material.

Figure 2B:
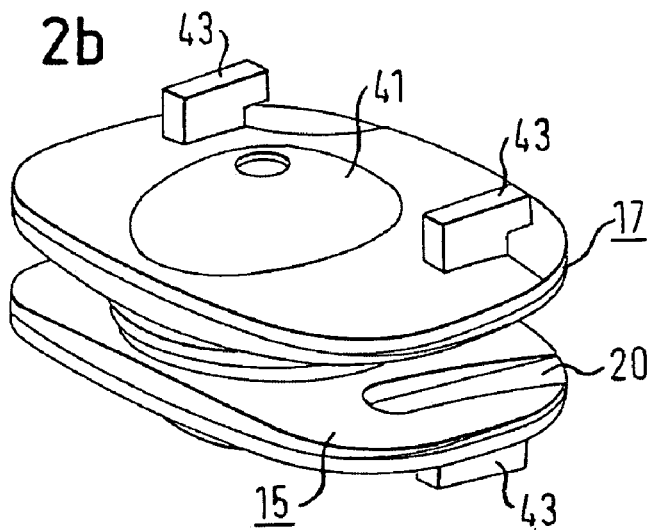
Figure 2C:
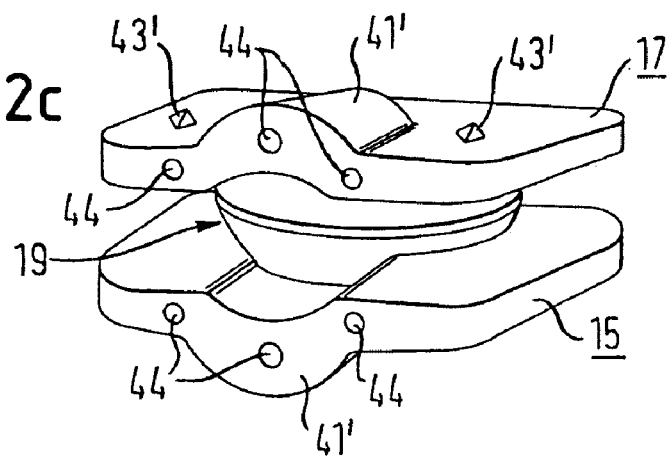
Figure 3A:
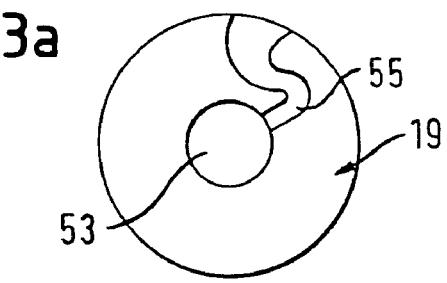
Figure 3B:
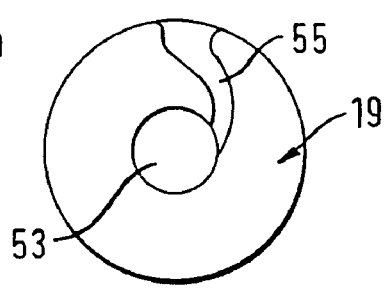
Figure 3C:
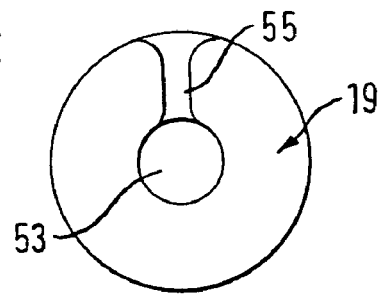
Figure 4:
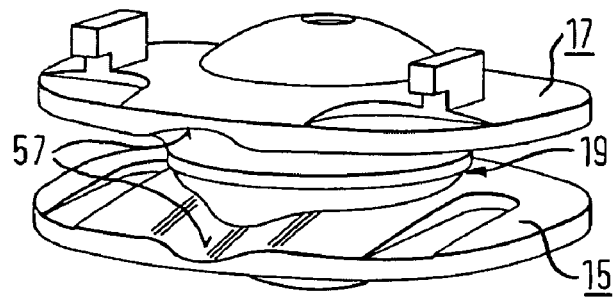
Figure 5:
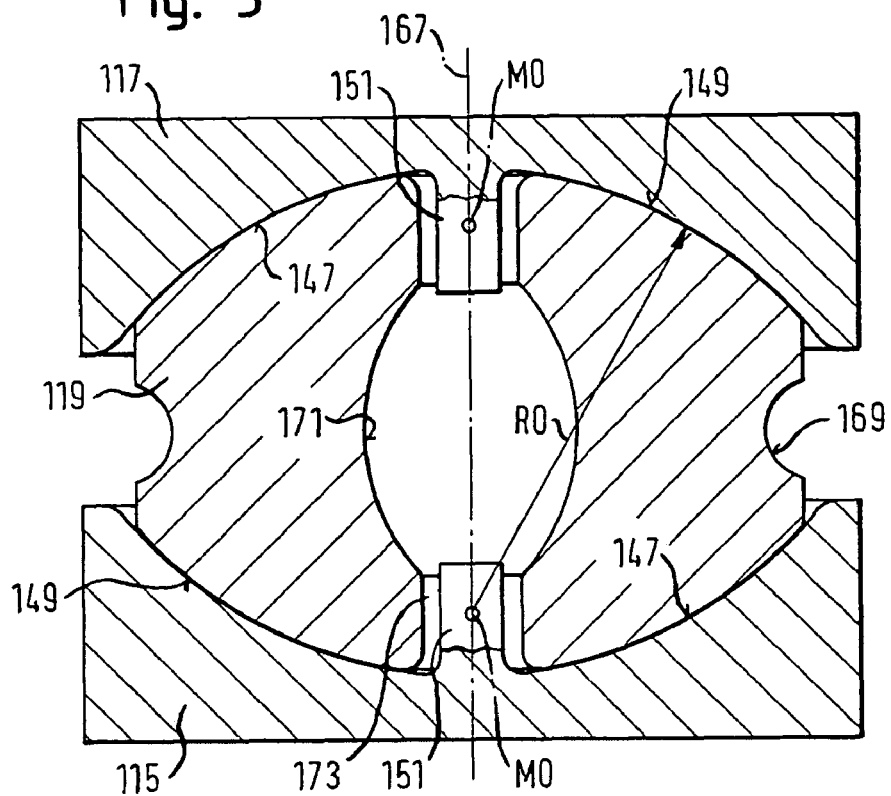
Figure 6:
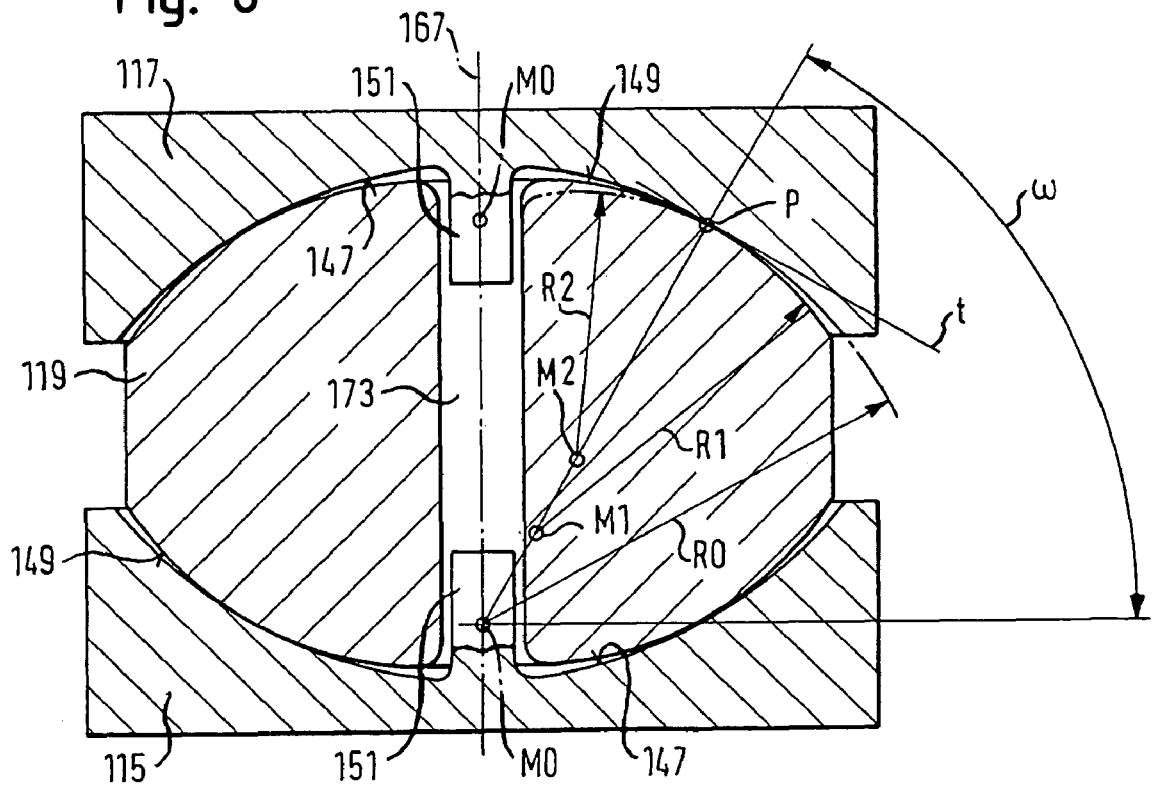

The invention will be described in the following by way of example with reference to the drawing. There are shown:

FIG. 1 different views of an intervertebral disk implant in accordance with the invention;

FIGS. 2*a*+2*b* different perspective views of the intervertebral disk implant of FIG. 1;

FIG. 2*c* an alternative embodiment of the intervertebral disk implant of FIG. 1 with respect to the implant plates;

FIGS. 3*a*-3*c* in each case a plan view of an embodiment of an implant core modified with respect to FIG. 1;

FIG. 4 a perspective view of an intervertebral disk implant modified with respect to FIG. 1;

FIG. 5 a further embodiment of an intervertebral disk implant in accordance with the invention;

FIG. 6 a further embodiment of an intervertebral disk implant in accordance with the invention; and FIGS. 7-12 further embodiments of an intervertebral disk implant in accordance with the invention.

FIG. 1 shows different views of a possible embodiment of an intervertebral disk implant in accordance with the invention which includes two implant plates 15, 17 also designated as cover plates or end plates as well as an implant core 19 also designated as an inlay. As already mentioned in the introductory part, the insertion of the intervertebral disk implant in accordance with the invention will be not looked at in more detail in this application. The likewise already mentioned European patent application EP 03 026 582 describes a spreading device in particular suitable for the intervertebral disk implants in accordance with the invention in accordance with FIGS. 1 to 4 of which some components will be mentioned in the following to the extent this is required for the understanding of the implants described in FIGS. 1 to 4.

The implant core 19 has a lens-like base shape which corresponds to two spherical segments contacting one another at their planar sides. The outer articulation surfaces 49 of the implant core 19 are thus part surfaces of a sphere. As can in particular be seen from the upper side view in FIG. 9, the shape of the implant core 19 does not precisely correspond to two spherical segments placed on top of one another, but a spacer 18 of relatively low height and with a straight rim is located between the planar sides of the spherical segments.

The implant core 19 is provided at its poles with depressions 53 into which spigots 51 of the implant plates 15, 17 project, when the implant is assembled, which will be considered in more detail in the following.

As can in particular be seen from sections B-B and C-C, the implant plates 15, 17 are each provided at their outer sides with a relatively shallow arch 63 on which a more strongly curved dome-shaped extension 41 in turn rises which corresponds to a recess 45 on the inner side of the implant plate 15, 17 whose articulation surface 47 is likewise a part surface of a sphere whose radius corresponds to that of the articulation surfaces 49 of the implant core 19. As in particular section C-C shows, there is full-area contact between the two articulation surfaces 47, 49 in the assembled state of the implant. For each spherical segment of the implant core 19, the centre point M of the sphere, on whose surface the articulation surfaces 47, 49 lie, lies within the respectively other spherical segment, and indeed in the region of the depression 53.

The implant plates 15, 17 are furthermore provided with peens 43 on their outer sides. The implant plates 15, 17 are guided at these guide projections 43 in groove-shaped recesses on the surfaces of the vertebral bodies previously prepared by means of a ball-peen hammer on insertion into the disk space.

Cut-outs 20 for the reception of an adapter element of a traction shoe are formed opposite the peens 43 on the inner sides of the implant plates 15, 17.

The variant in accordance with FIG. 2c differs from the implant shown in FIG. 1 and FIGS. 2a and 2b by the design of the outer sides of the implant plates 15, 17, which are here each provided with a barrel-shaped extension 41', whereby—in the inserted state—in turn a positional stability of the implant plates 15, 17 and additionally a longitudinal guidance is provided on the insertion of the implant plates 15, 17.

Instead of e.g. peen-like guide elements, spike-shaped holding projections 43' having a pyramid shape are moreover provided. The height of these acutely tapering projections 43' also known as pins is selected such that they do not disadvantageously influence the insertion of the implant plates 15, 17, but provide positional fixing, when the implant is inserted, in that they engage into the vertebral body surfaces facing one another. An optimum insertion behavior is achieved in that a respective edge of the pyramid-shaped pins 43' faces in the direction of insertion.

The implant in accordance with FIG. 2c is designed for a different surgical procedure and in particular for a different kind of insertion of the implant plates 15, 17 and of their spreading than the implant in accordance with FIG. 1 and FIGS. 2a and 2b. In particular different instruments are used which will not be looked at in more detail in the present application. Reference is made in this respect to the European patent application EP 04 024 653 filed on Oct. 15, 2004. The implant plates 15, 17 are each provided with bores 44 on their ventral side for the reception of corresponding projections of the setting devices for use with the instruments, in particular setting units, described in the said application.

The diameter of the spigots 51 of the implant plates 15, 17 provided in the form of separate elements (section C-C in FIG. 1) is smaller than that of the depressions 53 formed in the implant core 19. The spigots 51, which project with clearance into the depressions 53 in this manner, prevent the implant core 19 from slipping out of the reception space formed by the two recesses 45 on extreme body postures.

As in particular the section A-A in FIG. 1 shows, the shallow arches 63 on the outer sides of the implant plates 15, 17 in each case do not extend over the total periphery up to the plate edge. A planar rim region 65 extends over a partial periphery of the implant plates 15, 17.

The section A-A moreover shows that the so-called angulation of the implant plates 15, 17 is respectively measured with respect to a zero frequency 0 which is a plane which extends perpendicular to the center axes of the spigots 51 drawn as dashed lines. The resulting angulation angle α of the assembled implant at a specific relative position between the implant core 19 and the two implant plates 15, 17 is determined by the sum of the caudal angulation a1 and the cranial angulation α2.

It can be seen from the plan view and from section A-A that the center of the dome 41 and of the spigot 51 is eccentrically displaced toward posterior along the center line.

The intervertebral disk implant in accordance with the invention has specific characteristic values which can be varied on the manufacture of the implant for the optimization of the implant and for adaptation to the respective anatomy of the patient. These are in particular the following parameters whose definition can be seen from the respective different views of FIG. 1:

H height of the implant
B width of the implant
T depth of the implant I
d dome position
h dome height
z arch center
w arch height
a peen spacing
f peen height
v spacing of the cut-outs Corresponding parameters also exist analogously for the variant of FIG. 2c in which consequently the respective parameters d and h relate to the barrel 41' and the parameters a and f to the position or to the spacing and to the height of the pins 43' and the parameter v gives the spacing between the two outer bores 44 for the insertion instrument.

In contrast to the embodiment shown in FIG. 1, the spigots 51 can also be omitted. Such an alternative embodiment can in particular be considered when the recesses 45 are made or can be made in the implant plates 15, 17 such that they already provide sufficient extrusion security alone, i.e. prevent the implant core 19 from slipping out with adequate security.

The implant plates 15, 17 can be made from a CoCr alloy or from a titanium alloy and be coated on the outer bone side with porous titanium and, optionally, also with hydroxyapatite (HAC) in order to permit a particularly fast ongrowth of the bone in this manner. In practice, a set of differently sized implant plates 15, 17 is preferably available to achieve optimum matching to different patient anatomies. The implant plates 15, 17 can in particular differ from one another with respect to their width, depth and angulation.

The implant core 19 can consist, for example, of polyethylene, highly cross-linked PE, UHMWPE or metal, in particular a CoCrMo alloy. Polyethylene is the preferred material, since hereby axially acting forces can be absorbed better resiliently, i.e. a better axial damping property is present. To avoid any possible abrasion, a thin metallic shell can be laid over the plastic material. A combination of metallic part surfaces of a sphere then arises which can be manufactured in enormously high precision with respect to one another due to their spherical form. Such a metal/metal interplay is generally described in the European patent application 97903208.3 (publication number EP 0 892 627) to whose content reference is explicitly made to complement the disclosure of the present application.

By the countersunk arrangement of the implant core 19 in the concavities 45 of the implant plates 15, 17, a relatively large force transmission area is provided and thus a comparatively small surface load is achieved, with the risk of extrusion simultaneously being kept low.

The perspective representations of the implant in FIGS. 2a and 2b in particular show the cut-outs 20 formed on the inner sides of the implant plates 15, 17 for the traction shoes and the design of the outer sides of the implant plates 15, 17 with the dome 43 and the peens 43.

FIGS. 3a-3c and FIG. 4 show possible measures which can be taken at the implant core 19 (FIGS. 3a-3c) and at the inner sides of the implant plates 15, 17 (FIG. 4) in order to keep the degree by which the implant plates 15, 17 have to be pressed apart for the introduction of the implant core 19 as low as possible.

In accordance with FIGS. 3a-3c, an introduction passage 55 is formed in each case on the outer side of the implant core 19 extending from the rim of the implant core 19 up to the central depression 53. The introduction passage 55 can generally have an extent of any desired curvature and open either substantially radially (FIG. 3a) or tangentially (FIG. 3b) into the depression 53. Alternatively, the introduction passage 55 can have a straight-line radial extent (FIG. 3c).

On the introduction of the implant core 19 between the implant plates 15, 17, the spigots 51 project into the introduction passages 55 of the implant core 19 so that the spigots 51 are also not in the way of an implant core 19 to be introduced with a lower plate spacing.

Alternatively or additionally to the introduction passages 55 of the implant core 19, the implant plates 15, 17 are each provided on their inner sides with an introduction passage 57 in the form of a groove-like depression which extends from the anterior plate rim up to the recess 45, whereby in total an "introduction tunnel" for the implant core 19 is present which extends from the anterior side up to the reception space for the implant core 19. The implant core 19 has already partly been received in the introduction passages 57 at the start of the introduction process so that the implant plates 15, 17 have to be pressed apart from one another by less much.

On an operation for the insertion of the intervertebral disk implant in accordance with the invention, the preparation of the disk space takes place up to the time at which the operation system in accordance with the invention comes into use, as previously, i.e. the scraping of the natural intervertebral disk takes place without the operation system in accordance with the invention. A first preparation of the end plates of the vertebral bodies also takes place in particular with a so-called "sharp spoon" (e.g. Cobb) without using the work plates 11, 13 in accordance with the invention.

Subsequently to this first preparation of the disk space, an operation system can be used, for example, such as is described in the afore-mentioned European patent application EP 03 026 582.

FIGS. 5 and 6 show preferred embodiments for an intervertebral disk implant in accordance with the invention. It is common to both embodiments that the articulation surfaces 147 of the implant plates 115, 117 are each part surfaces of a sphere with a radius $R0$ and a center $M0$ lying on the center axis 167 of the implant and on a spigot 151 of the respectively other plate. Both implant cores 119 are moreover each made rotationally symmetrically and are provided with a central passage 173 whose longitudinal axis coincides with the center axis 167.

In the implant core 119 in accordance with FIG. 5, the articulation surfaces 149 are likewise part surfaces of a sphere with a radius $R0$ and a center $M0$ in accordance with the articulation surfaces 147 of the implant plates 115, 117 so that—analogously to the implant in accordance with FIG. 1—the articulation surfaces 147, 149 of the implant core 119 and of the implant plates 115, 117 contact one another over a full area.

In order to achieve an improved "spring effect" for the minimization of peak loads under the influence of pressure, as is explained in the introductory part, the implant core 119 is provided at the height of the equatorial plane with an outer ring groove 169 and an inner groove nut 171 which is substantially wider in comparison with the outer ring groove 169 and which in this respect represents a radial extension of the central passage 173.

In the implant core 119 in accordance with FIG. 6, a different approach was selected to achieve an improved support effect. The articulation surfaces 149 of the implant core 119 are here not part surfaces of a sphere shaped in accordance with the articulation surfaces 147 of the implant plates 115, 117. It is rather the case that the articulation surface 149 of the implant core 119 is shaped in each quadrant such that the implant core 119 and the implant plates 115, 117 only touch at a line P. In the cross-section shown here along the center axis 167, the position of the contact line P is selected such that a straight line extending through the center $M0$ and the point P, that is intersecting the tangent t through the point P at right angles, includes an angle of with the equatorial plane of the implant core 119 which amounts to approximately 60°. The angle $\alpha$ preferably lies in an angular range from approximately 45° to 75°.

FIG. 6 shows two preferred variants on the basis of this basic principle of a line contact between the implant core 119 and the implant plates 115, 117. In the variant shown with solid lines, the articulation surface 149 of the implant core 119 has a constant radius of curvature $R1 < R0$ with a center $M1$. A variant is shown by the double chain-dotted line in FIG. 6 in which, starting from the contact line P, the curvature of the articulation surface 149 of the implant core 119 is larger in the direction of the core pole than in the direction of the core equator, i.e. the radius of curvature $R2$ with the center $M2$ is smaller than the radius of curvature $R1$ with the center $M1$.

A preferred condition for these parameters is $R0-6 \text{ mm} < R1 < R0-1 \text{ mm}$, where $R2 < R1$ and $8 \text{ mm} < R0 < 18 \text{ mm}$.

In accordance with FIG. 6, provision is furthermore made in this embodiment for the centers $M0$, $M1$ and $M2$ to lie on a common straight line which intersects the contact line P marking the transition between the two articulation surface regions of the implant core 119.

In accordance with the invention, a combination of the specific articulation surface geometry in accordance with FIG. 6 with the ring groove approach in accordance with FIG. 5 is also basically possible, i.e. different measures which each result in a geometry of the implant core differing from a simple base shape can generally be combined with one another to achieve an improved "spring effect".

The implant cores described in this application and in particular in the following in connection with FIGS. 7 to 12 are in particular coordinated to an average central European with respect to their dimensions. The implant cores have a lens-shape with an outer diameter of approximately 25 mm and a height of approximately 19 mm which is provided by the flattening of a central passage extending in the axial direction. Furthermore, the implant cores are designed for a radius of curvature R0 of approximately 14 mm of the implant plates not shown in FIGS. 7 to 12.

It is furthermore common to all implant cores that the articulation surfaces of the implant core cooperating with articulation surfaces of the implant plates are part surfaces of a sphere with the mentioned radius of curvature R0 of approximately 14 mm. The lens shape of the implant cores is self-aligning in that the implant cores have at least approximately the shape of two spherical segments whose planar sides face one another, with the respective spherical center of the one spherical segment lying inside the other spherical segment.

Figure 7A:
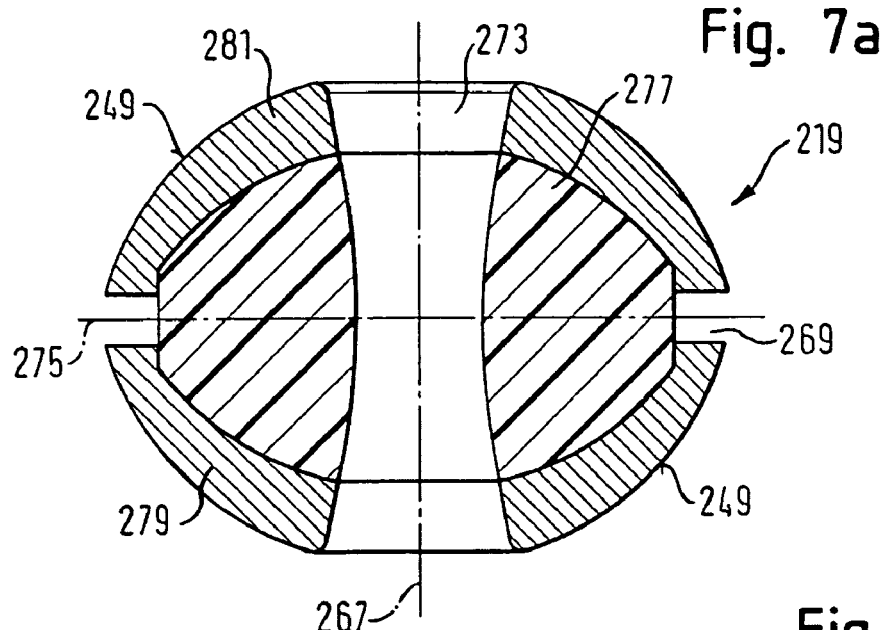

The implant core in accordance with FIGS. 7a and 7d includes an approximately lens-shaped support cushion 277 on which two half-shells 279, 281 lying spaced apart from and opposite to one another are arranged. The support cushion 277 consists of polycarbonate urethane (PCU), silicone or a PCU/silicone mix, whereas the two half shells 279, 281 are manufactured from polyethylene (PE), highly cross-linked PE, UHMWPE or metal, in particular a CoCrMo alloy. Both the support cushion 277 and the two half shells 279, 281 each had a ring shape due to a passage 273 which extends perpendicular to the equatorial plane 275 and whose center axis coincides with the center axis 267 of the implant core 219.

The half shells 279, 281 project beyond the support cushion 277 in the radial direction. In the region of this overhang or of this covering, a ring gap is present between the half shells 279, 281 axially spaced apart in this respect which forms a radially outer ring groove 269 of the implant core 219. This ring groove 269 can in particular be recognized in the perspective representation of FIG. 7b.

The articulation surfaces 249 of the implant core 219 formed by the outer sides of the half shells 279, 281 are part surfaces of a sphere and have the same radius of curvature as the articulation surfaces of the implant plates (not shown) of the intervertebral disk implants.

The radially outer side edge of the support cushion 277 extends parallel to the center axis 267, whereas the inner rim or inner side of the support cushion 277 bounding the central passage 273 is made in convex shape. This extent of the inner side of the support cushion 277 is continued by the inner rim region of the half shells 279, 281. The central passage 273 consequently has a shape in the axial section shown here of a double cone, a double funnel or an hourglass with a minimal free inner cross-sectional area in the equatorial plane 275.

Spigots of the implant plates project into the central passage 273 in the assembled state of the intervertebral disk implant, e.g. corresponding to the embodiments of FIGS. 5 and 6.

The support cushion 277 and the two half shells 279, 281 form a solid material composite which is manufactured by injection molding of the material used for the support cushion 277 (in particular PCU, silicone or a PCU/silicone mix) onto the half shells 279, 281 consisting in particular of PE highly cross-linked PE, UHMWPE or metal, in particular a CoCrMo alloy, as is described in the introductory part.

Thanks to its lens shape, the support cushion 277 provides a softer support for the half shells 279, 281 in its central range in the axial direction than in the radially outer rim region. This behavior can be influenced by the shape of the central passage 273. The actual support is transposed radially inwardly by the mentioned radial overhang of the half shells 279, 281, whereby the occurrence of pressure peaks in the radially outer rim region is avoided.

Figure 7B:
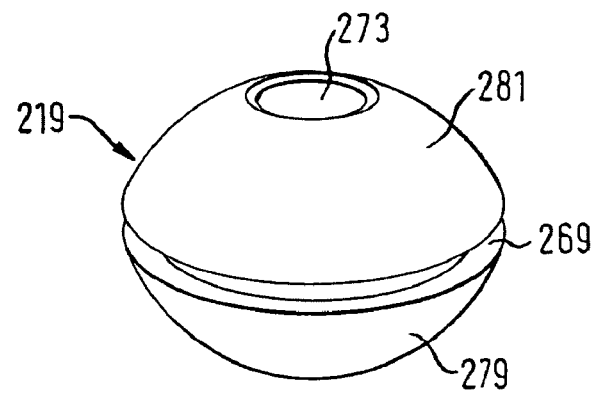
Figure 8:
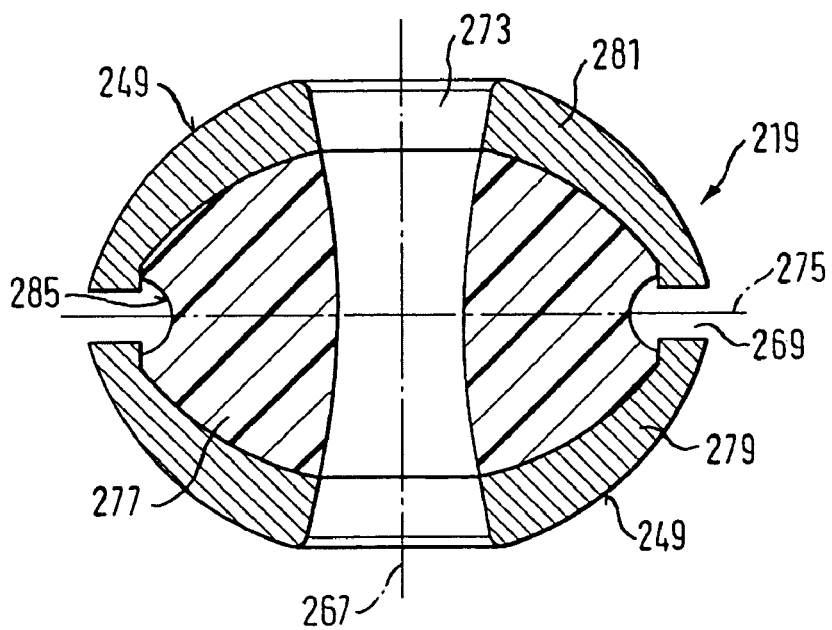

The implant core 219 in accordance with FIG. 8 differs from that of FIGS. 7a and 7b by the provision of an outer ring groove 285 formed in the support cushion 277 at the height of the equatorial plane 275. The extent of the reduction of the axial height of the support cushion 277 in the radially outer rim region can be set by such a restriction.

The ring groove 285 of the support cushion 277, together with the equatorial ring gap between the two half shells 279, 281, forms the outer ring groove 269 of the total implant core 219.

In the implant core 219 in accordance with the invention shown in FIGS. 9a-9c, the support cushion 277 terminates in a respectively flush manner downwardly and upwardly with a ring shaped intermediate layer 289, 291 made of metal. The outer diameter of the intermediate rings 289, 291 extending parallel to the equatorial plane 275 amounts to approximately 60% of the outer diameter of the outer PE half shells 279, 281, whereas the inner diameter of the intermediate rings 289, 291 amounts to approximately 24% of the outer diameter of the half shells.

In each case starting from the ring shaped intermediate layers 289, 291, the diameter of the support cushion 277 increases in the direction of the equatorial plane 275, with a respective intermediate space 283 becoming outwardly wider, however, being present radially outside the intermediate layers 289, 291 between the support cushion 277 and the half shells 279, 281. The half shells 279, 281 are consequently only supported via the metal rings 289, 291 at the support cushion 277.

The support cushion 277 forms, with the metal intermediate rings 289, 291, a solid material composite which is manufactured at the inner sides of the intermediate layers 289, 291 by injection molding of the material provided for the support cushion 277 for which e.g. the aforesaid materials are considered. An additional shape-matched connection is created by undercut bores 295 which are formed in the intermediate layers 289, 291 and into which the material of the support cushion 277 flows during manufacture. As FIG. 9c shows, a plurality of circular undercuts 295 are provided which are arranged at a uniform spacing from one another.

As the detail "C" of FIG. 9a shows, the side edges of the intermediate rings 289, 291 and the radially outer bounding sides of reception regions formed in the half shells 279, 281 are undercut such that a respective snap-connection can be established between the composite of support cushion 277 and intermediate rings 289, 291, on the one hand, and the two half shells 279, 281, on the other hand. The half shells 279, 281 can therefore simply be clipped onto the support cushion 277 fixedly connected to the metal rings 289, 291.

Figure 10A:
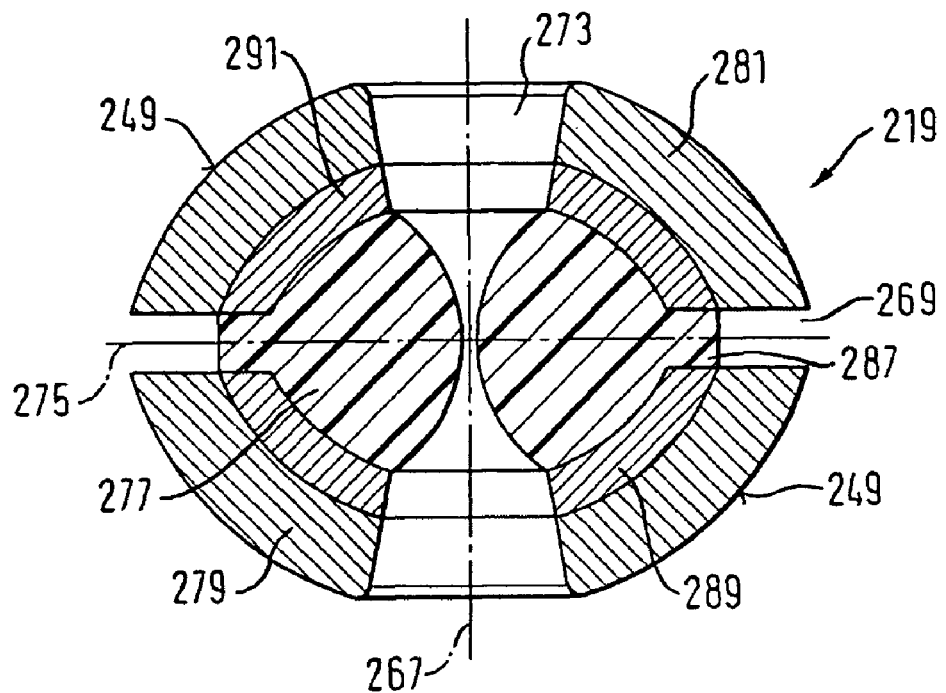
Figure 10B:
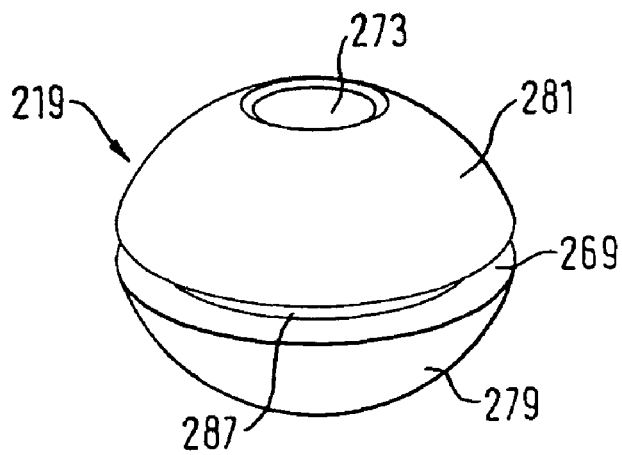

In the embodiment of FIGS. 10a and 10b, ring-shaped intermediate layers 289, 291 are in turn arranged between the support cushion 277 made of PCU and the PE shells 279, 281. In this embodiment, the intermediate rings 289, 291 do not, however, extend perpendicular to the center axis 267 of the implant core 219, but are rather curved in accordance with the outer half shells 279, 281 providing the articulation surfaces 249.

The radial inner side of the ring-shaped support cushion 277 has a comparatively strong convex curvature, with the central passage 273 having a pronounced narrowing in the equatorial plane 275.

In the radial direction, the support cushion 277 terminates in a flush manner with the intermediate rings 289, 291 via a flange-like section 287 lying between the intermediate metal rings 289, 291. The PE half shells 279, 281 therefore in turn have an overhang with respect to the composite of support cushion 277 and intermediate rings 289, 291. The half shells 279, 281 each terminate in the axial direction in a flush manner with the intermediate rings 289, 291, whereby the implant core 219 has an outer ring groove 269 whose axial height corresponds to the thickness of the flange section 287 of the support cushion 277.

The connection between the intermediate layers 289, 291 made from a CoCrMo alloy and the PE half shells 279, 281 takes place in each case by injection molding of the PE material onto the outer sides of the metal intermediate layers 289, 291 which are provided for this purpose with recesses or undercuts (not shown in FIG. 10a) into which the PE material can flow during injection molding. These undercuts are preferably provided in the form of circular, recessed steps whose width and height vary with the radial position such that the step width reduces and the step height increases from the inside to the outside. This manufacture of the material composite can basically also be used with other material pairs, that is it is not limited to PE for the half shells and a CoCrMo alloy for the intermediate layers.

It is preferred for the embodiments of FIGS. 9 and 10 for the spigots (cf. FIGS. 5 and 6) projecting from the implant plates (not shown here) and protruding into the central passage 273 to extend up to the metallic intermediate layers 289, 291 since then, with tilt movements of the implant plates taking place relative to the implant core 219 due to the articulation, the metal rings 289, 291 can serve as path boundaries for the spigots and thus the implant plates without impairing the PE half shells 279, 281.

Figure 11A:
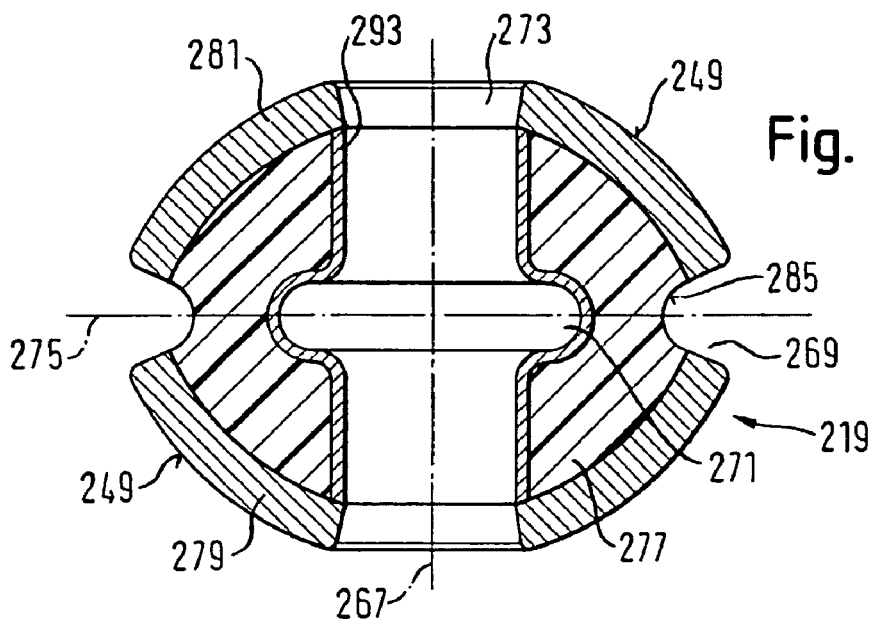
Figure 11B:
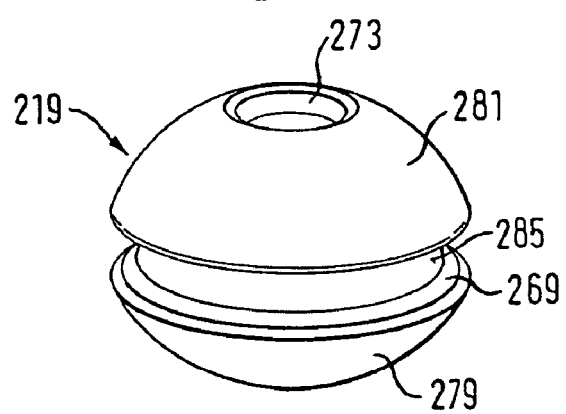

The implant core 219 in accordance with FIGS. 11a, 11b does not have any intermediate layers between the support cushion 277 again made of PCU and the outer half shells 279, 281 which are not made of PE in this embodiment, but of metal. The connection between the PCU support cushion 277 and the half shells 279, 281 takes place by injection molding of the PCU material.

At its radial inner side, the support cushion 277 is supported by a stiffening element 293 which is made as metal bellows and which extends up to the inner sides of the metal half shells 279, 281. On the one hand, the stiffness of the support cushion 277 in the axial direction is hereby increased. On the other hand, an improved guide of the half shells 279, 281 relative to one another results due to the stiffening element 293, whereby it is prevented that the half shells 279, 281 "float" on the support cushion 277.

The half shells 279, 281 and the stiffening element 293 are preferably made from the same material for which in particular a CoCrMo alloy is used.

The wall thickness of the half shells 279, 281 lies in an order of approximately 1 mm, whereby sufficient shape resilience results. A resulting support of the half shells 279, 281 in the central region between a radially outer ring groove 285 of the support cushion 277 and the inner side, i.e. the stiffening element 293, permits a comparatively small change of shape of the half shells 279, 281 in the radially outer rim region in the order of μm in the axial direction.

The outer ring groove 285 of the support cushion 277 and the ring gap between the half shells 279, 281 axially spaced apart in this respect together form an outer ring groove 269 of the total implant core 219. An inner ring groove 271 is created by a radially outwardly directed bulging of the metal bellows 293 at the height of the equatorial plane 275.

The articulation surfaces 249 (formed by part surfaces of a sphere) of the half shells 279, 281 made of metal in this embodiment and the corresponding articulation surfaces of the implant plates (not shown) can be processed—when the spigots of the implant plates (cf. e.g. FIGS. 5 and 6) are subsequently attached to the implant plates e.g. by pressing in—by means of the method already mentioned in the aforesaid European patent application with the publication number EP 0 892 627 with that precision which is required to achieve the desired reduction in the surface pressing in these rim regions via the shape resilience of the radially outer rim regions of the half shells 279, 281.

Figure 11C:
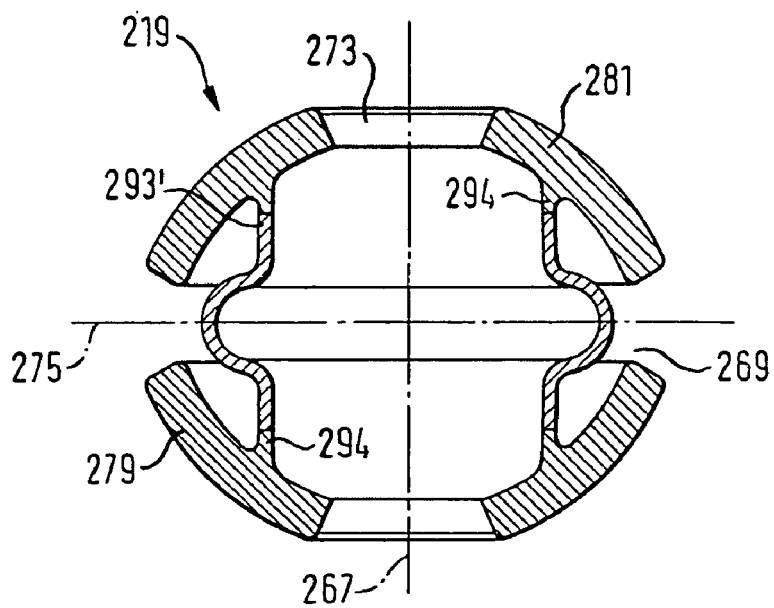

Alternatively to the embodiment shown in FIGS. 11a and 11b, in accordance with a further variant of the invention shown in FIG. 11c, the support cushion can also be omitted and the support of the half shells 279, 281 can take place exclusively via a stiffening element 293', e.g. corresponding to the bellows 293 in accordance with FIG. 11a. In this variant, the stiffening element 293' is offset radially outwardly, i.e. provided with a larger diameter, with respect to the position shown in FIG. 11a. As a result, the support of the half shells 279, 281 takes place in a central region—in which the half shells 279, 281 each have an axial ring projection for the stiffening element 293'—between the radially outer margin, on the one hand, and the inner margin bounding the central passage 273 or the central openings of the ring-shaped half shells 279, 281, on the other hand, whereby pressure peaks are in turn avoided in these radially outer and inner rim regions.

Figure 12A:
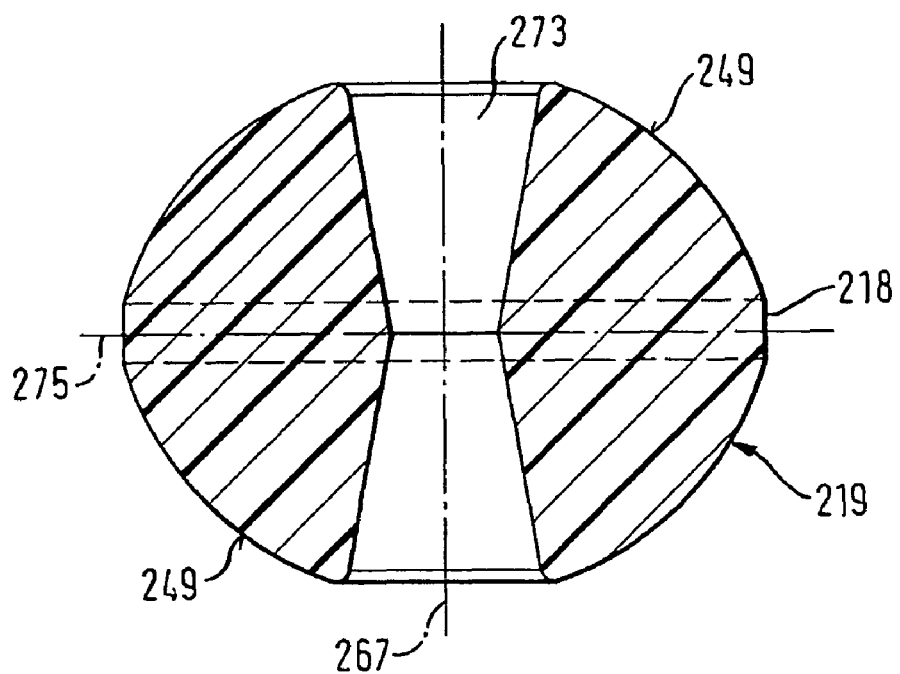
Figure 12B:
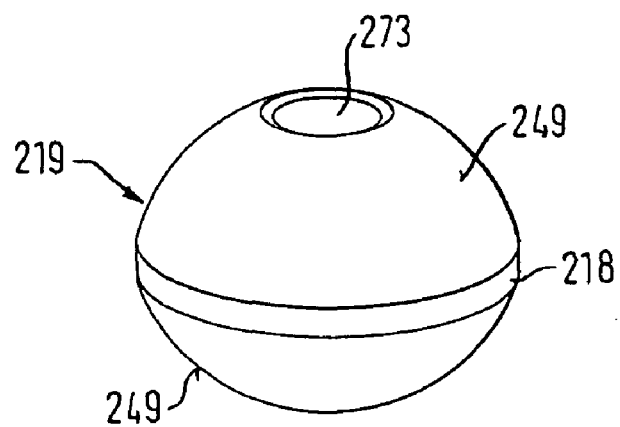

In the embodiment of FIGS. 12a and 12b, the implant core 219 is only formed by a PCU support cushion which is provided with a central passage 273 symmetrical to the equatorial plane 275 in the form of a double cone converging in the equatorial plane 275.

The implant core 219 has the shape of two spherical segments whose planar sides face one another and a cylindrical disk 218 disposed therebetween. The axial height of this cylindrical disk 218 is selected such that the part surfaces of a sphere (not shown) of the implant plates cooperating with the articulation surfaces 249 of the implant core 219 cover the cylinder disk 218, i.e. still have a sufficiently large overhang, in every permitted articulation position.

Compression takes place under load due to the comparatively high resilience of the PCU material forming the implant core 219 not only in the axial direction, but also in the radial direction, whereby the axially outer rim region of the articulation surfaces 249 is reduced. A reduction of the pressure load of the articulation surfaces 249 in the direction of the axially outer rim regions consequently also occurs with coinciding radii of curvature R0 between the implant core 219 and the implant plates.

The pressure distribution adopted under load can also be set directly toward the radially inner side by the shape of the central passage 273 which is of double cone shape here.

The articulation surfaces 249 of the PCU implant core 219 can additionally be provided with a cross-link and/or a coating which serves to reduce the wear. In this process, the wear reduction can be achieved by a higher strength and/or by a lower friction value.

The implant cores 219 explained above with reference to FIGS. 7 to 12 have the following dimensions, with reference moreover being made to the introductory part in this respect:

The smallest inner diameter of the ring-shaped support cushion 277, i.e. the diameter of the central passage 273 at the narrowest restriction disposed in the equatorial plane 275 amounts to approximately 5 mm in the examples of FIGS. 7, 8 and 9, to approximately 0.4 mm in the example of FIG. 10 and to approximately 4 mm in the example of FIG. 12.

The largest diameter of the central passage 273 at the outer side of the half shells 279, 281 or of the implant core 219 amounts to approximately 7.4 mm in the examples of FIGS. 7 and 8 and to approximately 7.3 mm in the example of FIG. 12.

The spacing between the centers of the spherical segments defining the part surfaces of a sphere 249 amounts to approximately 6 mm in the examples of FIGS. 7, 8 and 11 and to approximately 5 mm in the example of FIG. 12.

The opening angle of the central passage 273 at the outer side of the half shells 279, 281 amounts to approximately 20° in the examples of FIGS. 7 and 8.

The axial height of the radially outer ring gap between the half shells 279, 281 amounts to approximately 2 mm in the examples of FIGS. 7, 8 and 10. In the example of FIG. 11, the smallest spacing between the half shells 279, 281 and thus the maximum axial width of the outer ring groove 285 of the support cushion 277 (FIGS. 11a and 11b) amounts to approximately 2.6 mm.

In the example of FIG. 9, the axial spacing between the metal rings 289, 291, i.e. the axial height of the support cushion 277, amounts to approximately 8 mm and the diameter of the central passage 273 at the height of the outer sides of the metal rings 289, 291 amounts to approximately 6 mm. The thickness of the metal rings 289, 291 amounts to approximately 1 mm.

In the example of FIG. 10, the wall thickness of the ring-shaped intermediate layers 289, 291 amounts to approximately 1.7 mm. The diameter of the central passage 273 at the maximum axial height of the support cushion 277, i.e. the smallest diameter of the intermediate rings 289, 291, amounts to approximately 6 mm.

In the example of FIGS. 11a and 11b, the inner diameter of the stiffening element 293 amounts to approximately 6.7 mm, whereas its wall thickness—also in the example of FIG. 11c—amounts to approximately 0.5 mm.

Reference Numeral List 15, 115 implant plate
17, 117 implant plate
18, 218 intermediate disk
19, 119, 219 implant core
20 cut-out for the adapter element
41, 41' dome shaped or barrel shaped extension
42 abutment pin
43, 43' guide projection, peen or holding projection
44 bore
45 recess of the implant plate
47, 147 articulation surface of the recess or implant plate
49, 149, 249 articulation surface of the implant core
51, 151 spigot
53 cut-out
55 introduction passage of the implant core
57 introduction passage of the implant plate
59 fluid line
61 vertebral body
63 arch
65 rim region
M spherical center
R radius of the articulation surfaces
0 zero reference
α angulation
H height of the implant plates
B width of the implant plates
T depth of the implant plates
d dome position
h dome height
z arch center
w arch height
a peen spacing
f peen height
v spacing of the cut-outs
167, 267 center axis of the implant core
169, 269 outer ring groove
171, 271 inner ring groove
173, 273 central passage
M0, M1, M2 center
R0, R1, R2 radius of curvature
P contact line
t tangent
ω angle
275 equatorial plane
277 support cushion
279 half shell
281 half shell
283 intermediate space
285 outer ring groove of the support cushion
287 flange section of the support cushion
289 intermediate layer
291 intermediate layer
293, 293' stiffening element
294 ring projection
295 recess, undercut

The invention claimed is:

1. An intervertebral disk implant, having two implant plates for contacting prepared vertebral body surfaces in the implanted state and an implant core which can be introduced between the implant plates, wherein the implant has an implant radius which corresponds to a radius of curvature (R0) of articulation surfaces of the implant plates and is measured from a center (M0) disposed on a central axis of the implant core, wherein the implant core in a resting state is made rotationally symmetrically with respect to the central axis and each articulation surface of the implant core has a radius of curvature (R1, R2) in a cross-section through the central axis, each of said radius of curvature (R1, R2) being smaller than the radius of curvature (R0) of the articulation surfaces of the implant plates, wherein R1 is not equal to R2, wherein a center (M1, M2) of each articulation surface of the implant core is spaced apart from the central axis.

2. An intervertebral disk implant in accordance with claim 1, characterized in that the centers M0, M1 and M2 of the radii of curvature R0, R1 and R2 lie on a common straight line which intersects the contact line P between the implant core and the implant plates, when the intervertebral disk implant is assembled, and which includes an angle GO with the equatorial plane of the implant core in the range from approximately 45° to 75°, in particular from at least approximately 60°.

3. An intervertebral disk implant in accordance with claim 1, characterized in that R0−6 mm<R1<R0−1 mm and/or R2<R1 applies, where R0 is the radius of curvature of the articulation surfaces of the implant plates.

4. An intervertebral disk implant in accordance with claim 1, characterized in that 8 mm<R0<18 mm applies, where R0 is the radius of curvature of the articulation surfaces of the implant plates.

5. An intervertebral disk implant in accordance with claim 1, characterized in that the implant core has a basic shape of a lens.

6. An intervertebral disk implant in accordance with claim 1, characterized in that the implant core has at least approximately the shape of two spherical segments whose planar sides lie on top of one another, with the respective spherical center of the one spherical segment lying within the other spherical segment.

7. An intervertebral disk implant in accordance with claim 1, characterized in that the implant core has at least approximately the shape of two spherical segments whose planar sides face one another and a cylindrical disk disposed therebetween, with the respective spherical center of the one spherical segment lying within the other spherical segment.

8. An intervertebral disk implant in accordance with claim 1, characterized in that the implant core is provided, in particular in the region of its equatorial plane, with either (1) an outer ring groove and with an inner ring groove, or (2) an outer ring groove or an inner ring groove, preferably forming a radial extension of a passage extending perpendicular to the equatorial plane.

9. An intervertebral disk implant in accordance with claim 1, characterized in that the implant core has a passage extending perpendicular to the equatorial plane whose longitudinal axis preferably coincides with the central axis of the implant core.

10. An intervertebral disk implant in accordance with claim 1, characterized in that the implant core is made in multiple parts and in particular includes an arrangement preferably made as a material composite of at least one inner support cushion and at least one shell surrounding the support cushion.

11. An intervertebral disk implant in accordance with claim 10, characterized in that the support cushion has a lens-like base shape.

12. An intervertebral disk implant in accordance with claim 10, characterized in that the shell includes two half shells which are preferably arranged spaced apart from one another in the axial direction.

13. An intervertebral disk implant in accordance with claim 10, characterized in that the support cushion and the shell are made from different materials, with the material of the shell preferably being harder and/or stiffer than the material of the support cushion.

14. An intervertebral disk implant in accordance with claim 10, characterized in that the shell projects beyond the support cushion in the radial direction.

15. An intervertebral disk implant in accordance with claim 10, characterized in that an intermediate space is present in a radially outer rim region between the shell and the support cushion.

16. An intervertebral disk implant in accordance with claim 10, characterized in that an intermediate layer, in particular made of metal, is arranged between the support cushion and the shell.

17. An intervertebral disk implant in accordance with claim 16, characterized in that the intermediate layer is made as a path boundary for spigots of the implant plates projecting into a passage extending perpendicular to an equatorial plane.

18. An intervertebral disk implant in accordance with claim 10, characterized in that a passage has a restriction bounded by an inner wall of the support cushion.

19. An intervertebral disk implant in accordance with claim 10, characterized in that the support cushion is made in ring shape, with the ring thickness measured in the radial direction preferably being the largest in the equatorial plane and in each case reducing with increasing axial distance from the equatorial plane.

20. An intervertebral disk implant in accordance with claim 10, characterized in that the support cushion is stiffened in a central region in the axial direction.

21. An intervertebral disk implant in accordance with claim 10, characterized in that the support cushion is stiffened inwardly in the radial direction.

22. An intervertebral disk implant in accordance with claim 10, characterized in that a separate stiffening element, in particular having a ring shaped or cylindrical base shape, is provided which is preferably arranged in a passage extending perpendicular to an equatorial plane.

23. An intervertebral disk implant in accordance with claim 10, characterized in that the support cushion is injection molded onto the shell, in particular onto two half shells forming the shell, with the material of the support cushion preferably having a higher melting point than the material of the shell for the forming of a material composite between the support cushion and the shell which can be manufactured by injection molding.

24. An intervertebral disk implant in accordance with claim 10, characterized in that the support cushion is injection molded onto an intermediate layer, in particular made of metal.

25. An intervertebral disk implant in accordance with claim 10, characterized in that the support cushion or an intermediate layer connected to the support cushion and in particular made of metal is connected to the shell in particular to two half shells forming the shell by a clip, snap, or latch connection.

26. An intervertebral disk implant in accordance with claim 1, characterized in that a passage of the implant core extending perpendicular to an equatorial plane has a cross-sectional area which varies over its length, with the cross-sectional area preferably respectively increasing, in particular constantly, outwardly from the equatorial plane.

27. An intervertebral disk implant in accordance with claim 1, characterized in that the implant plates each have a dome-shaped extension, in particular in the form of a spherical segment, or a barrel-shaped extension at their outer side.

28. An intervertebral disk implant in accordance with claim 1, characterized in that the outer sides of the implant plates are each outwardly arched, with the arches preferably being provided in addition to a dome-shaped extensions or a barrel-shaped extension.

29. An intervertebral disk implant in accordance with claim 1, characterized in that the outer sides of the implant plates each have a planar rim region extending at least over part of the periphery of the implant plates.

30. An intervertebral disk implant in accordance with claim 1, characterized in that the implant plates each have at least one guide projection formed as a peen and a holding projection or formed as a peen or a holding projection, in particular a pyramid-shaped holding projection, on their outer side.

31. An intervertebral disk implant in accordance with claim 1, characterized in that the implant plates each have a recess on their inner sides for the reception of the implant core.

32. An intervertebral disk implant in accordance with claim 1, characterized in that at least one implant plate has a spigot which protrudes from its inner side and which projects into a depression formed on the outer side of the implant core, when the implant is assembled, with the depression being dimensioned larger than the spigot in order to permit a relative movement between the implant plate and the implant core.

33. An intervertebral disk implant in accordance with claim 32, characterized in that the spigot is arranged centrally with respect to the dimension of the implant plate in the sagittal direction.

34. An intervertebral disk implant in accordance with claim 32, characterized in that the spigot is arranged eccentrically with respect to the dimension of the implant plate in the sagittal direction.

35. An intervertebral disk implant in accordance with claim 1, characterized in that the implant core is provided on at least one outer side with an introduction passage for the spigot of the implant plate extending from the rim to the depression.

36. An intervertebral disk implant in accordance with claim 1, characterized in that at least one implant plate is provided on its inner side with an introduction passage for the implant core extending from the rim to the recess.

37. An intervertebral disk implant in accordance with claim 1, characterized in that the implant core has a greater resilience in a radially outer rim region than in a radially inner central region.

38. An intervertebral disk implant in accordance with claim 1, characterized in that the implant core has the lowest resilience in a radially central region which is disposed between a radially outer region, on the one hand, and a central region provided with a passage extending perpendicular to an equatorial plane, on the other hand.

* * * * *